(12) United States Patent
Zhang

(10) Patent No.: US 11,364,397 B2
(45) Date of Patent: Jun. 21, 2022

(54) DOUBLE-LAYER LIGHT-TRANSMISSIVE FACE MASK

(71) Applicant: Yuejie Zhang, Frankfort, IL (US)

(72) Inventor: Yuejie Zhang, Frankfort, IL (US)

(73) Assignee: Yuejie Zhang, Frankfort, IL (US)

( * ) Notice: Subject to any disclaimer, the term of this patent is extended or adjusted under 35 U.S.C. 154(b) by 0 days.

(21) Appl. No.: 17/601,643

(22) PCT Filed: May 10, 2021

(86) PCT No.: PCT/US2021/031506
§ 371 (c)(1),
(2) Date: Oct. 5, 2021

(87) PCT Pub. No.: WO2021/231256
PCT Pub. Date: Nov. 18, 2021

(65) Prior Publication Data
US 2022/0096879 A1     Mar. 31, 2022

Related U.S. Application Data

(60) Provisional application No. 63/025,934, filed on May 15, 2020.

(51) Int. Cl.
*A62B 23/02*     (2006.01)
*A41D 13/11*     (2006.01)
(Continued)

(52) U.S. Cl.
CPC .............. *A62B 23/02* (2013.01); *A41D 13/11* (2013.01); *A61F 9/029* (2013.01); *A62B 18/084* (2013.01)

(58) Field of Classification Search
CPC .............. A62B 23/00–025; A62B 7/10; A41D 13/11–1192
See application file for complete search history.

(56) References Cited

U.S. PATENT DOCUMENTS 2,665,686 A * 1/1954 Wood ...................... A61F 9/028
2/9
3,042,034 A * 7/1962 Gruenewaelder ...... A41D 13/11
128/206.12
(Continued)

FOREIGN PATENT DOCUMENTS

CN      102038299 A     5/2011
JP      2009011475 A    1/2009
(Continued)

OTHER PUBLICATIONS

Search Report and Written Opinion for International Patent Application No. PCT/US21/31506, dated Aug. 16, 2021.
(Continued)

*Primary Examiner* — Rachel T Sippel
(74) *Attorney, Agent, or Firm* — Marshall, Gerstein & Borun LLP

(57) ABSTRACT

A face mask includes an outer layer, an inner layer, and a filter. The outer layer includes an outer front guard constructed from a light-transmissive material and an outer filtering surface extending posteriorly from the outer front guard that includes at least one outer air hole. The inner layer is nestled within the outer layer. The inner layer includes an inner front guard constructed from a light-transmissive material and separated from the outer front guard by a buffer space. The inner layer also includes an inner filtering surface extending posteriorly from the inner front guard that includes at least one inner air hole. A filter is positioned between the outer filtering surface and the inner filtering surface and covers the at least one outer air hole and the at least one inner air hole.

18 Claims, 4 Drawing Sheets

(51) Int. Cl.
*A61F 9/02* (2006.01)
*A62B 18/08* (2006.01)

(56) References Cited

U.S. PATENT DOCUMENTS

| | | | |
|---|---|---|---|
| 4,467,799 A | | 8/1984 | Steinberg |
| 4,630,604 A | * | 12/1986 | Montesi ............. A41D 13/1146 |
| | | | 128/206.17 |
| 6,354,296 B1 | | 3/2002 | Baumann et al. |
| 10,888,130 B1 | | 1/2021 | Naos |
| 10,945,469 B1 | | 3/2021 | Rosenberg et al. |
| 10,974,084 B1 | * | 4/2021 | Grinvald ............. A62B 18/025 |
| 2003/0029454 A1 | | 2/2003 | Gelinas et al. |
| 2006/0230485 A1 | | 10/2006 | Lee |
| 2008/0092897 A1 | | 4/2008 | Behm et al. |
| 2010/0319105 A1 | | 12/2010 | Fairbanks |
| 2012/0325221 A1 | * | 12/2012 | Tran ..................... A62B 23/025 |
| | | | 128/206.17 |
| 2013/0014316 A1 | | 1/2013 | Castro et al. |
| 2016/0030779 A1 | | 2/2016 | Twu et al. |
| 2016/0316831 A1 | | 11/2016 | Yarahmadi |
| 2019/0358473 A1 | * | 11/2019 | Szasz ................... G08B 21/182 |
| 2020/0121005 A1 | | 4/2020 | Belousov et al. |
| 2021/0307413 A1 | * | 10/2021 | Scalisi ............... A41D 13/1161 |
| 2021/0339062 A1 | * | 11/2021 | Vasudeva ............. A62B 18/006 |
| 2021/0393140 A1 | * | 12/2021 | Rein ....................... A61B 5/015 |

FOREIGN PATENT DOCUMENTS

| | | |
|---|---|---|
| JP | 2009189676 A | 8/2009 |
| WO | WO-2006034227 A2 | 3/2006 |

OTHER PUBLICATIONS

Carscoops, "Ford Develops Clear N95 Face Marsks". Retrieved from the Internet at: <https://www.youtube.com/watch?v=d6w5S_T7bZA> on Feb. 2, 2021.
ClearMask™, "Transparent Face Mask". Retrieved from the Internet at: <https://buy.theclearmask.com/collections/consumer/products/clearmask-bulk> on May 10, 2021.
Locewell, "Eyelet Adjustable Mouth Clear Window Visible Face Mask". Retrieved from the Internet at: <https://locewell.com/products/hfr630-loce> on May 10, 2021.
4AllPromos, "Promo Reusable 6" Face Shield". Retrieved from the Internet at: <https://www.4allpromos.com/product/reusable-6-face-shield> on May 10, 2021.
Safe 'N' Clear, "The Communicator™ Facemask". Retrieved from the Internet at: <https://safenclear.com/> on May 10, 2021.
Oirental Trading, "Adult's Face Masks with Clear Plastic Window—6 pc". Retrieved from the Internet at: <https://www.orientaltrading.com/adult-s-face-masks-with-clear-plastic-window-6-pc--a2-13953018.fltr> on May 10, 2021.
Totobobo®, "Totobobo Mask for Kids (Small) (USD)". Retrieved from the Internet at: <https://www.totobobohk.com/product/totobobo-mask-for-kids-tt-02-small> on May 10, 2021.
Walmart, "Clarity Face Shield for Adults". Retrieved from the Internet at: <https://www.walmart.ca/fr/ip/TiooDre-3-Pack-Clarity-Face-Shield-For-Adult-Anti-Fog-Masks-Reusable-Clear-Mask-Transparent-All-Bandanas-Breathable-Washable-Comfortable-Visible-Expr/3T6U36QZIHGJ> on May 10, 2021.
Walmart, "CAYU 1pcs Durable Face Shield Transparent Safety Face Shield Home Oil-Splash Proof Mask Protection Cover Facial Protection". Retrieved from the Internet at: <https://www.walmart.ca/fr/ip/CAYU-1pcs-Durable-Face-Shield-Transparent-Safety-Face-Shield-Home-Oil-Splash-Proof-Mask-Protection-Cover-Facial-Protection/4MG0MLF836YU> on May 10, 2021.
Kung Pao, Takungpao, "Science and Technology Anti-epidemic/ Technology University develops nano-film to make transparent masks". Dec. 22, 2020.
"Clear Face Shield". Retrieved from the Internet at: <https://shopee.tw/%E5%BE%AE%E7%AC%91%E5%8F%A3%E7%BD%A9-%E9%80%8F%E6%98%8E%E5%8F%A3%E7%BD%A9-%E9%98%B2%E9%A3%9B%E6%B2%AB-%E9%98%B2%E9%9C%A7%E9%80%8F%E6%B0%A3-%E5%A1 %91 %E8%86%A0%E5%8F%A3%E7%BD%A9-%E9%A4%90%E9%A3%B2-%E7%99%BE%E8%B2%A8-%E5%BB%9A%E5%B8%AB-%E5%B0%88%E7%94%A8%E5%8F%A3%E7%BD%A9-%E7%92%B0%E4%BF%9D%E8%A1 %9B%E7%94%9F(V50-2285)-i.14101879.1454939113> on May 10, 2021.
"Reusable Face Shield Image". Retrieved from the Internet at: <https://www.google.com/imgres?imgur=https://wx1.sinaimg.cn/orj480/0074w9gggy1gf96d7gdklj30mh0u046r.jpg&imgrefurl=https://s.weibo.com/weibo?q%3D%2523%25E6%2584%258F%25E5%25A4%25A7%25E5%2588%25A9%25E9%2580%258F%25E6%2598%258E%25E5%258F%25A3%25E7%25BD%25A9%2523%26from%3Ddefault&h=641&w=480&tbnid=YdZAFWFWjqvPPM&tbnh=260&tbnw=194&usg=AI4_-kQypC41wE0GV8ezDDdmpaa8lazKTg&vet=1&docid=dLpjlSLXQKN07M&itg=1 &hl=en> on May 10, 2021.
Totobobo, "Hightech reusable respirator mask". Retrieved from the Internet at: <https://totobobo.com/blog/users/for-children/> on May 10, 2021.

* cited by examiner

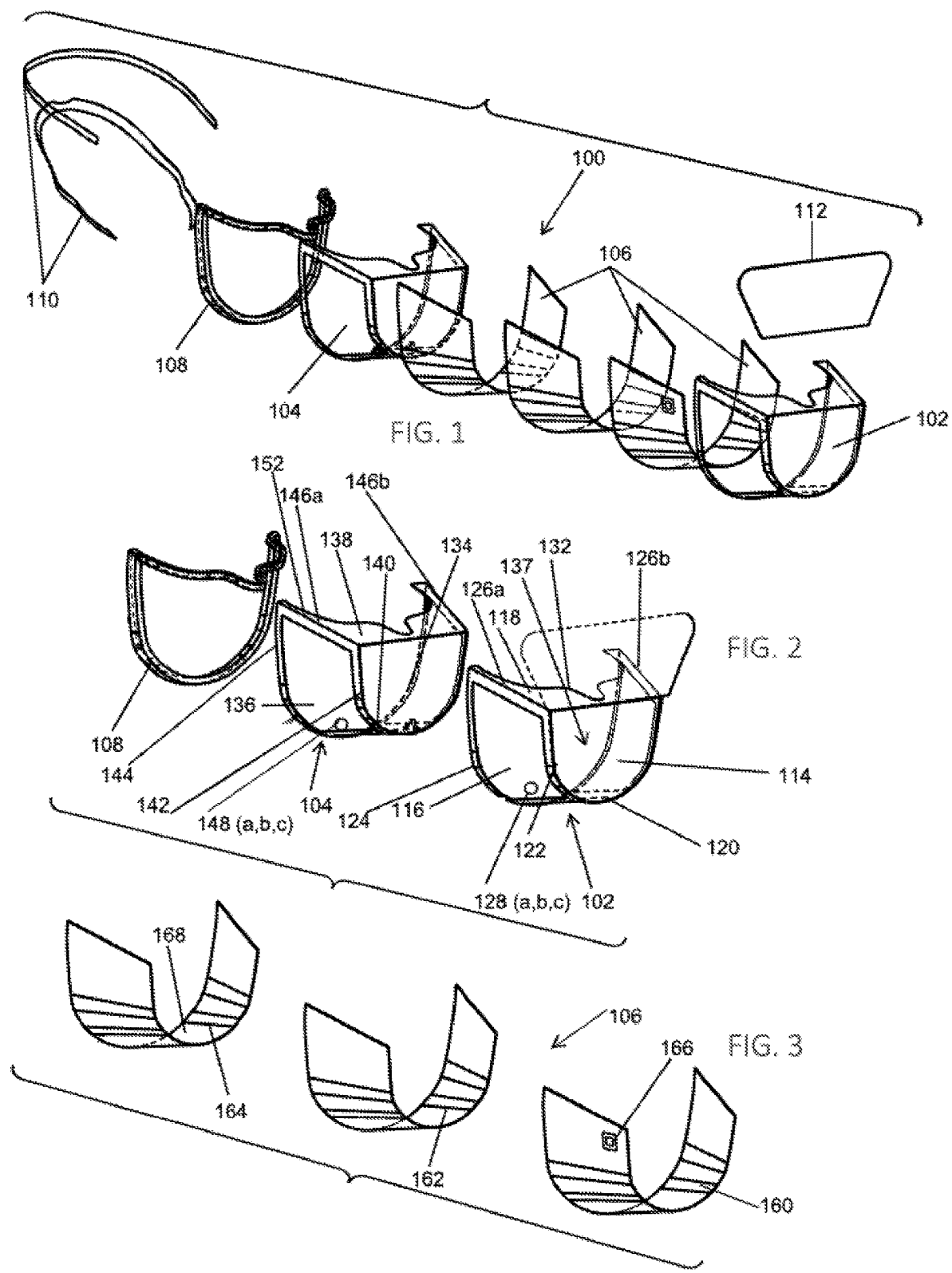

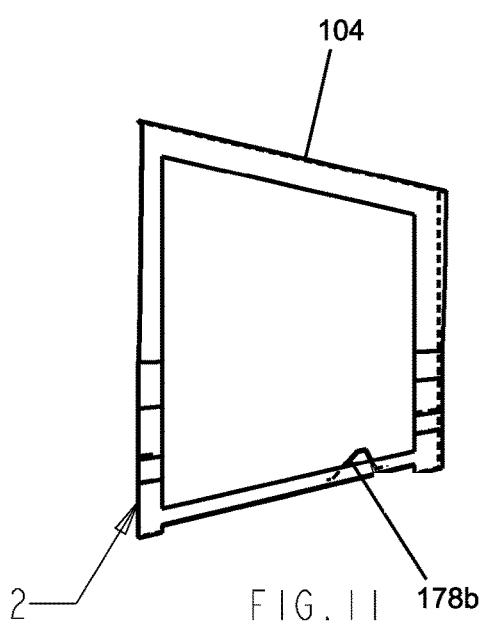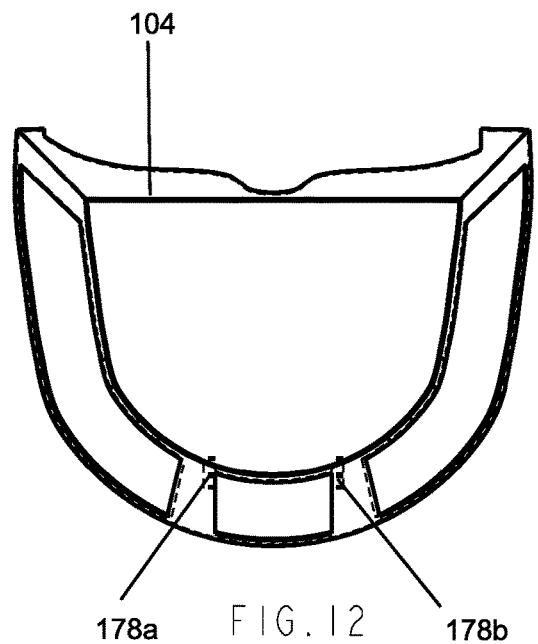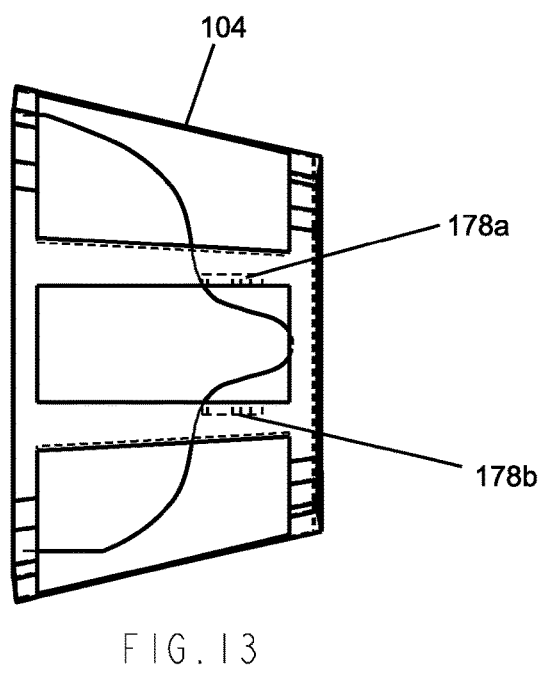

DOUBLE-LAYER LIGHT-TRANSMISSIVE FACE MASK

CROSS-REFERENCE TO RELATED APPLICATIONS

This application is a national stage application of PCT/US21/31506 filed May 10, 2021 and entitled "Double-Layer Light-Transmissive Face Mask," and which claims the benefit of the filing date of U.S. Provisional Application No. 63/025,934 filed May 15, 2020 and entitled "A Dual Visible Covers Mask with a Scan Code," the entirety of which are herein expressly incorporated by reference.

FIELD OF THE INVENTION

The present disclosure relates to personal protective equipment for protection from airborne pathogens, and specifically relates to a multi-layer light-transmissive face mask.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Existing surgical and N95 masks are deficient in a variety of ways. Some masks fail to adequately seal against the face of a wearer, which results in leaks causing dangerous exposure to pathogens. For example, many masks are not airtight along the sides of the mask. Some masks require the filtering material of the mask to be in contact with a wearer's face, which can be irritating to those with sensitive skin. Most masks are not designed to accommodate an eye shield without causing fogging problems. Many masks cannot be decontaminated easily and are intended as single-use products, which is costly and wasteful. Multi-use masks typically have a reusable body with a replaceable filter, but replacing the filter poses a risk of contamination. Facial expressions and visual cues are critical to high quality communication, but existing surgical and N95 masks typically cover the mouth of the wearer, impairing the ability of a wearer to communicate. Masks designed with a transparent window to improve communication result in a decrease in the surface area of the filter, thereby increasing breath resistance and moisture accumulation, both of which make wearing the mask less comfortable. Masks with a transparent window also typically include heavy frames that consume more material than a typical mask and therefore have a negative environmental impact.

SUMMARY

The present design for a face mask remedies the deficiencies discussed above. In particular, the face mask described herein is light-transmissive, enabling non-verbal communication and facilitating identification of the wearer, while still maintaining a filter surface area of sufficient size that breath resistance and moisture accumulation do not increase. The face mask does not require a frame and can be used multiple times without requiring a filter change. The face mask may be sealed against the face of a wearer without requiring filter material to come into contact with skin. Furthermore, the face mask can be used in conjunction with an eye shield to provide more robust protection without causing fogging problems.

In accordance with an example, a face mask includes an outer layer, an inner layer, and a filter. The outer layer has an outer front guard constructed from a light-transmissive material. The outer layer also has an outer filtering surface connected to and extending posteriorly from the outer front guard. The outer filtering surface includes at least one outer air hole and a first face-adjacent edge. The outer layer still further has an outer top connected to the outer front guard and the outer filtering surface. The outer top includes a first nose-adjacent edge. The outer front guard, the outer filtering surface, and the outer top define an outer volume. The inner layer is nestled within the outer volume of the outer layer. The inner layer has an inner front guard separated from the outer front guard by a buffer space. The inner front guard is constructed from a light-transmissive material. The inner layer also has an inner filtering surface connected to and extending posteriorly from the inner front guard. The inner filtering surface includes at least one inner air hole and a second face-adjacent edge aligned with the first face-adjacent edge to form a combined face-adjacent edge. Additionally, the inner layer includes an inner top connected to the inner front guard and the inner filtering surface. The inner top includes a second nose-adjacent edge aligned with the first nose-adjacent edge to form a combined nose-adjacent edge. The filter is positioned between the outer filtering surface and the inner filtering surface. The filter covers the at least one outer air hole and the at least one inner air hole. The raised mask creates more space around the cheek and chin by increasing the space between a wearer's face and the inner front guard. The increased space not only increases the effective filtering area but also reduces breathing resistance pressure. The double layer regulates a temperature difference between the inside of mask and the outside to reduce fog formation.

In some forms, the filter may have a filtering surface area greater than or equal to 100 centimeters squared. The filter may comprise a plurality of layers of nonwoven fabric. The plurality of layers may include an inner filter layer, a middle filter layer, and an outer filter layer. The face mask may include a scan code printed on the outer filter layer and visible through the outer filtering surface. The outer filtering surface may taper conically outward from the outer front guard to the first face-adjacent edge. The inner filtering surface may taper conically outward from the inner front guard to the second face-adjacent edge.

In other forms, the inner layer may further comprise a chin stop extending superiorly from the inner filtering surface and adapted to engage a chin of a wearer. The chin stop may be a first chin stop, and the inner layer may further comprise a second chin stop extending superiorly from the inner filtering surface, the second chin stop offset laterally from the first chin stop and also adapted to engage the chin of the wearer.

In still other forms, the inner front guard and the outer front guard may be arranged in parallel planes such that the buffer space is located between the parallel planes. A buffer distance may extends perpendicularly between the parallel planes across the buffer space is greater than or equal to one millimeter.

In some forms, the face mask may further comprise a securement strap operably engaged with at least one of the outer layer and the inner layer to secure the face mask on a wearer. The securement strap may include an upper strap and a lower strap. The outer layer may be ultrasonically welded to the inner layer.

In other forms, a seal may extend along the combined face-adjacent edge and the combined nose-adjacent edge. The combined nose-adjacent edge and the combined face-adjacent edge together may form a mask perimeter, and the length of the mask perimeter may be selected from a set of size options in order to accommodate a face size of a wearer of the mask. The combined nose-adjacent edge may comprise a nose contour having a shape adapted to be flush against a nose of the wearer, the shape selected from a set of shape options in order to accommodate the nose shape of the wearer. The combined nose-adjacent edge may further comprises two symmetric check contours.

In still other forms, the face mask may comprise an eye shield extending superiorly from the outer layer planar with the outer front guard.

BRIEF DESCRIPTION OF THE DRAWINGS

The figures described herein depict various aspects of the system and methods disclosed herein. It should be understood that each figure depicts an example of aspects of the present systems and methods.

FIG. 1 is an exploded view of an example face mask of the present disclosure, the face mask including an outer layer, an inner layer, a seal, an eye shield, securement straps, and a three-layer filter.

FIG. 2 is an exploded view of just the outer layer, the eye shield, the inner layer, and the seal depicted in FIG. 1.

FIG. 3 is an exploded view of the three-layer filter of FIG. 1.

FIG. 11 is a side view of the inner layer of FIG. 9.

FIG. 12 is a front view of the inner layer of FIGS. 9 and 11.

FIG. 13 is a bottom view of the inner layer of FIGS. 9, 11, and 12.

Figure 5:
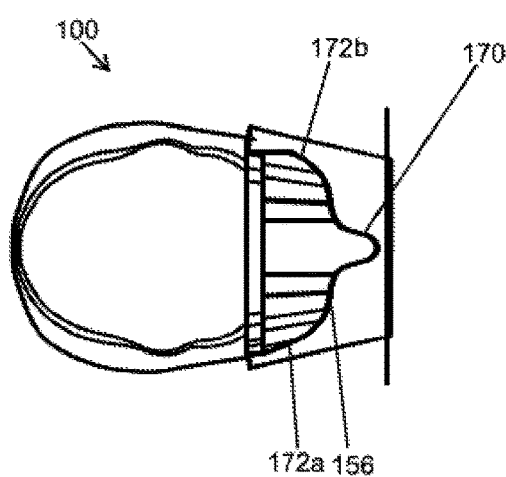
FIG. 5 is a top view of the example face mask of FIGS. 1 and 4.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

FIG. 1 illustrates a face mask 100 in an unassembled, exploded view. The face mask 100 includes an outer layer 102, an inner layer 104 configured to nest within the outer layer 102, and a filter 106 including three layers and configured for placement between the outer layer 102 and the inner layer 104. In addition to these components, the face mask 100 includes a seal 108, a securement strap 110, and an eye shield 112.

Figure 10:
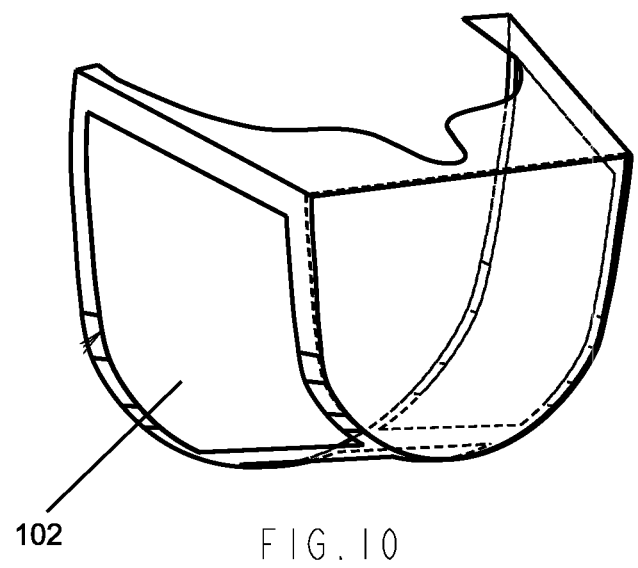
FIG. 10 is an isometric view of the outer layer of FIGS. 1 and 2.

As shown in FIG. 2 (as well as in FIG. 10), the outer layer 102 includes an outer front guard 114, an outer filtering surface 116, and an outer top 118. In FIG. 2, the outer front guard 114 is U-shaped with the U-shape formed by an outer front guard edge 120. In other arrangements within the scope of this disclosure, the outer front guard 114 may have a different shape formed by the outer front guard edge 120 including but not limited to a semi-circular shape, a rectangular shape, an eccentric shape, or any other shape providing suitable front coverage of a wearer's face. The outer front guard 114 is constructed from a light-transmissive material. Optimally, the outer front guard 114 is constructed from a light-transmissive material that is translucent or clear. The light-transmissive material may be thin to minimize material waste and facilitate light transmission.

As further shown in FIG. 2, the outer filtering surface 116 has an outer filtering surface edge 122 connected to the outer front guard 114 at the outer front guard edge 120. The outer filtering surface 116 extends posteriorly from the outer front guard 114. In particular, as shown in FIG. 2, the outer filtering surface 116 tapers conically outward from the outer front guard before terminating at a first face-adjacent edge 124. The outer filtering surface 116 has side boundaries 126a and 126b that extend from the outer filtering surface edge 122 to the first face-adjacent edge 124. The outer filtering surface 116 thus has a surface area defined by a perimeter including side boundary 126a, first face-adjacent edge 124, side boundary 126b, and outer filtering surface edge 122. The outer filtering surface 116 includes at least one outer air hole 128. The outer air hole 128 may be one or more large openings or may include a plurality of small perforations (128a, 128b, 128c . . . ) distributed across the outer filtering surface 116. The small perforations (128a, 128b, 128c . . . ) may be distributed uniformly or at random or may be localized within select areas of the outer filtering surface 116.

As further shown in FIG. 2, the outer top 118 is connected to the outer front guard 114 at the outer front guard edge 120. The outer top 118 is also connected to the outer filtering surface 116 at side boundaries 126a and 126b. In addition, the outer top 118 has a first nose-adjacent edge 132 that is free from any connections to the outer front guard 114 and the outer filter surface 116. The first nose-adjacent edge 132 is curved in a manner that is complementary to the shape of a wearer's face. In particular, the first nose-adjacent edge 132 is curved to accommodate the projection of a wearer's nose.

FIG. 2 shows that the outer front guard 114, the outer filtering surface 116, and the outer top 118 define an outer volume 137 that the inner layer 104 is configured to nestle within. Much like the outer layer 102, the inner layer 104 includes an inner front guard 134, an inner filtering surface 136, and an inner top 138. In FIG. 2, the inner front guard 134 is U-shaped with the U-shape formed by an inner front guard edge 140. In other arrangements within the scope of this disclosure, the inner front guard 134 may have a different shape formed by the inner front guard edge 140 including but not limited to a semi-circular shape, a rectangular shape, an eccentric shape, or any other shape providing suitable front coverage of a wearer's face. In the arrangement shown in FIG. 2, the inner front guard 134 has the same shape as the outer front guard 114 but is slightly smaller to enable the inner layer 104 to nestle within the outer layer 102. In other arrangements not depicted herein, the inner front guard 134 may have a different shape than the outer front guard 114 but must be sized to enable the inner layer 104 to nestle within the outer layer 102. Like the outer front guard 114, the inner front guard 134 is constructed from a light-transmissive material. Optimally, the inner front guard 134 is constructed from a light-transmissive material that is translucent or clear. The light-transmissive material may be thin to minimize material waste and facilitate light transmission. Because both the inner front guard 134 and the outer front guard 114 are light-transmissive, and in some cases translucent or clear, the face of a wearer of the face mask 100 is visible through the inner front guard 134 and the outer front guard 114. This enables a wearer of the face mask 100 to provide non-verbal communication easily and also to be easily identified.

As further shown in FIG. 2, the inner filtering surface 136 has an inner filtering surface edge 142 connected to the inner front guard 134 at the outer front guard edge 140. The inner filtering surface 136 extends posteriorly from the inner front guard 134. In particular, as shown in FIG. 2, the inner filtering surface 136 tapers conically outward from the inner front guard 134 before terminating at a second face-adjacent edge 144. The second face-adjacent edge 144 is curved in a manner substantially identical to the first face-adjacent edge 124 of the outer layer 102. The inner filtering surface 136 has side boundaries 146a and 146b that extend from the inner filtering surface edge 142 to the second face-adjacent edge 144. The inner filtering surface 136 thus has a surface area defined by a perimeter including side boundary 146a, second face-adjacent edge 144, side boundary 146b, and inner filtering surface edge 142. The inner filtering surface 136 includes at least one inner air hole 148. The inner air hole 148 may be one or more large openings or may include a plurality of small perforations (148a, 148b, 148c . . . ) distributed across the inner filtering surface 136. The small perforations (148a, 148b, 148c . . . ) may be distributed uniformly or at random or may be localized within select areas of the outer filtering surface 116. The inner air hole 148 or holes (148a, 148b, 148c . . . ) may or may not be aligned with the outer air hole 128 or holes (128a, 128b, 128c . . . ) when the face mask 100 is assembled.

As further shown in FIG. 2, the inner top 138 is connected to the inner front guard 134 at the inner front guard edge 140. The inner top 138 is also connected to the inner filtering surface 136 at side boundaries 146a and 146b. In addition, the inner top 138 has a second nose-adjacent edge 152 that is free from any connections to the inner front guard 134 and the inner filter surface 136. The second nose-adjacent edge 152 is curved in a manner that is complementary to the shape of a wearer's face. In particular, the second nose-adjacent edge 152 is curved to accommodate the projection of a wearer's nose. The second nose-adjacent edge 152 is curved in a manner substantially identical to that of the first nose-adjacent edge 132.

Figure 4:
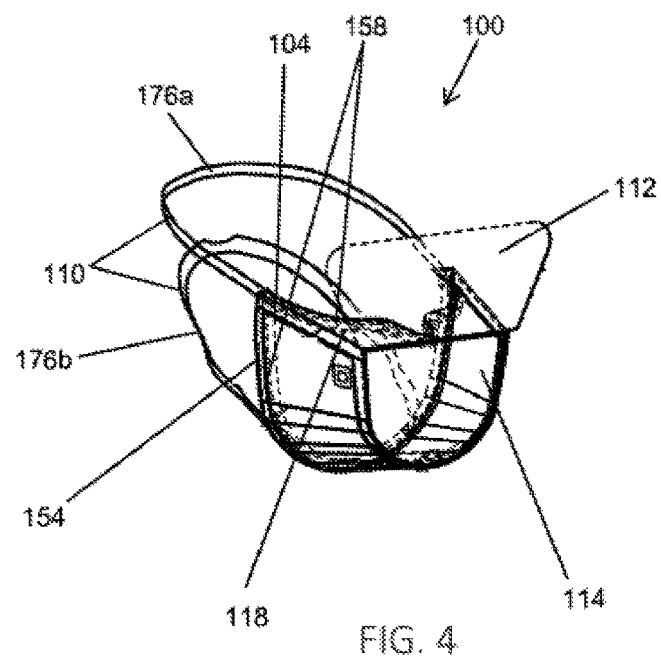
FIG. 4 is a front isometric view of the example face mask of FIG. 1 fully assembled.

When the inner layer 104 is assembled with the outer layer 102, the first face-adjacent edge 124 of the outer layer 102 and the second face-adjacent edge 144 of the inner layer 104 are substantially flush and combine to form a combined face-adjacent edge 154 (shown in FIG. 4). Similarly, the first nose-adjacent edge 132 of the outer layer 102 and the second nose-adjacent edge 152 of the inner layer 104 are substantially flush and combine to form a combined nose-adjacent edge 156 (shown in FIG. 5). The combined nose-adjacent edge 156 and the combined face-adjacent edge 154 together form a mask perimeter 158 (shown in FIG. 4), and the length of the mask perimeter 158 is chose from a set of size options in order to accommodate a face size of a wearer of the face mask 100. For example, the mask perimeter 158 may have a length selected from a set of size options identified as small, medium, large, and extra large. As another example, the set of size options may include size options identified as child-size, adolescent-size, and adult-size.

The seal 108 shown in FIG. 2 (and shown alone in FIG. 8) extends along the mask perimeter 158 (shown in FIG. 4) when the face mask 100 is assembled. The seal 108 may be constructed from hypoallergenic silicone, rubber, sponge, synthetic materials, or known skin-friendly materials. The seal 108 may be configured to prevent other parts of the face mask 100, such as the outer layer 102, inner layer 104, and filter 106 from contacting the skin of the wearer, thereby preventing skin irritation. The seal 108 ensures that the face mask 100 fits snugly against a wearer's face in order to prevent leaks that might cause contamination.

Turning to FIG. 3, the filter 106 is shown in an exploded illustration. In the arrangement depicted in FIG. 3, the filter 106 includes a plurality of layers of nonwoven fabric. In particular, the filter 106 includes an inner filter layer 160, a middle filter layer 162, and an outer filter layer 164. In other arrangements not depicted herein, the filter 106 may have only one or two layers or may have more than three layers. The filter 106 may include a scan code 166 for purposes of identification or sale. In the arrangement depicted, the scan code 166 is printed on the outer filter layer 164 and is visible through the outer filtering surface 116 (as shown in FIG. 4). In other arrangements, the scan code 166 may be located in a different location. For example, the scan code 166 may be printed on the inner filter layer 160 and visible through the inner filtering surface 136 when the mask is unworn by a wearer.

When the face mask 100 is assembled, the filter 106 is positioned between the outer filtering surface 116 and the inner filtering surface 136 and covers the at least one outer air hole 128 or holes (128a, 128b, 128c . . . ) as well as the at least one inner air hole 148 or holes (148a, 148n, 148c). Due to the unique arrangement of the outer filtering surface 116 and the inner filtering surface 136 relative to the outer front guard 114 and the inner front guard 134, the filter 106 has a filter surface area 168 that is equal in size to the surface area of filters in masks that do not have light-transmissive components. This means that the filter 106 is able to perform the important task of decontaminating air that flows through it without causing an uncomfortable increase of moisture or air flow resistance within the face mask 100. The size of the filter surface area 168 may vary depending on the size of the face mask 100. For example, if the face mask 100 is child-sized, the filter surface area 168 may be greater than or equal to 100 centimeters squared. If the face mask 100 is adult-sized, a minimum size of the filter surface areal 68 may be more than 100 centimeters squared.

Figure 6:
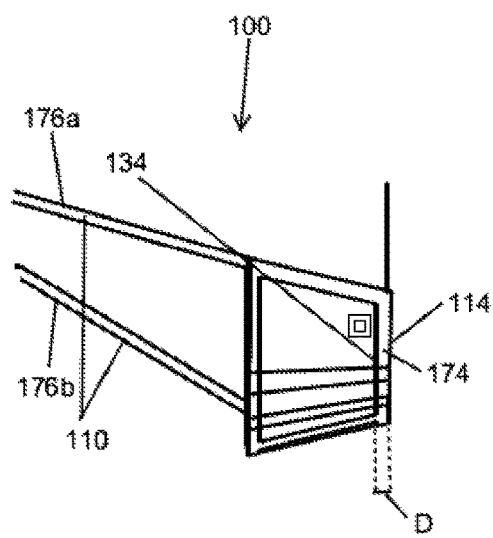
FIG. 6 is a side view of the example face mask of FIGS. 1, 4, and 5.
Figure 7:
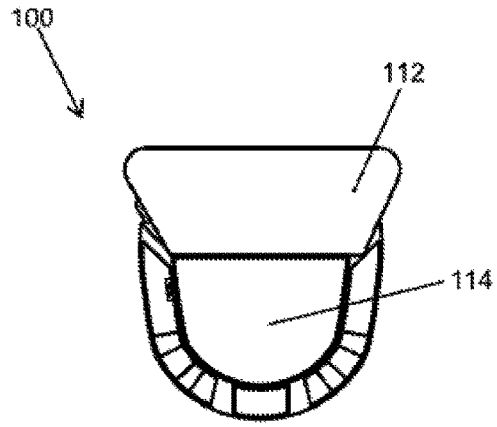
FIG. 7 is a front view of the example face mask of FIGS. 1 and 4-6.

FIG. 4 illustrates the face mask 100 once assembled. FIGS. 5, 6, and 7 show top, side, and front views of the assembled face mask 100. The outer layer 102 (shown in FIG. 10) is connected to the inner layer 104 (shown in FIG.

9) by a friction fit, adhesive, fastener, or other connection methods. For example, the outer layer 102 may be ultrasonically welded to the inner layer 104. As best shown in FIG. 5, the combined nose-adjacent edge 156 includes a nose contour 170 and two symmetric cheek contours 172a and 172b. The nose-contour 170 is adapted to be flush against a nose of the wearer and may be selected from a set of shape options in order to accommodate the nose shape of the wearer. For example, the set of shape options may include shapes having different widths and depths to accommodate different nose shapes. Likewise, the symmetric check contours 172a and 172b may be selected from a set of shape options that accommodate different cheek contours.

As best shown in FIG. 6, the inner front guard 134 and the outer front guard 114 are separated by a buffer space 174. More specifically, as shown in FIG. 5, the inner front guard 134 and the outer front guard 114 are arranged in substantially parallel planes such that the buffer space 174 is located between the parallel planes. A buffer distance D extending perpendicularly between the parallel planes across the buffer space is greater than or equal to one millimeter. In other arrangements not depicted, the inner front guard 134 and the outer front guard 114 may be disposed at an angle relative to one another with the buffer space 174 disposed between. Whatever the arrangement, the buffer space 174 provides the important benefit of preventing fogging without requiring any chemical substances be applied to the inner front guard 134 or the outer front guard 114.

The securement strap 110 is best shown in FIGS. 4 and 6. The securement strap 110 is connected to the inner layer 104. The securement strap 110 may alternately be connected to the outer layer 102. The connection between the securement strap 110 and the inner layer 104 or the outer layer 102 may be direct or indirect via a fastener or intermediate part. In the arrangement best shown in FIGS. 4 and 6, the securement strap 110 includes an upper strap 176a and a lower strap 176b. In other arrangements not depicted, the securement strap 110 may only include one strap or may include more than two straps. The securement strap 110 depicted in FIGS. 4 and 6 is intended to wrap fully around a wearer's head but alternate arrangements may be design to wrap only around a wearer's ears.

As best shown in FIGS. 4 and 7, the face mask 100 includes an eye shield 112 adapted to partially protect a wearer's eyes and upper head from direct exposure to fluid flow. The eye shield may be connected to the outer top 118 in the same plane as the outer front guard 114. The eye shield 112 may be permanently connected or may be removable in order to be used at a wearer's discretion. Beneficially, because the outer air hole 128 or holes (128a, 128b, 128c . . . ) shown in FIG. 2 direct the outflow of air from within the face mask 100 away from the eye shield 112, and because the seal 108 prevents air outflow anywhere except the outer air hole 128 or holes (128a, 128b, 128c . . . ), the eye shield 112 does not experience the fogging that commonly occurs when a shield is used in conjunction with a face mask.

Figure 8:
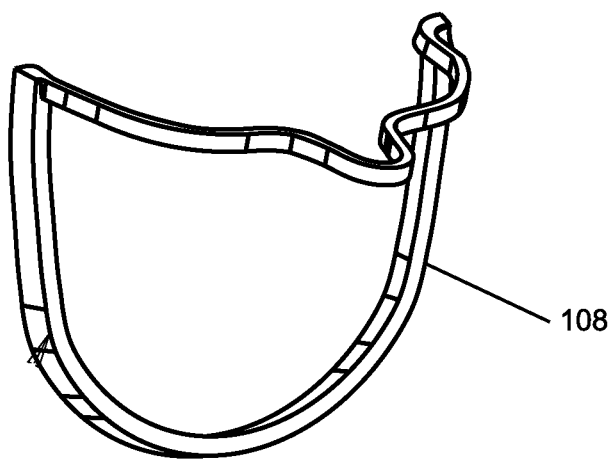
FIG. 8 is an isometric view of the seal of FIGS. 1 and 2.

FIG. 8 illustrates the seal 108, which functions as a gasket to prevent airflow into or out of the face mask 100 where the face mask 100 is pressed against a wearer's face. In addition to the material discussed above, the seal 108 may include a cloth covering in order to increase comfort and decrease skin irritation.

Figure 9:
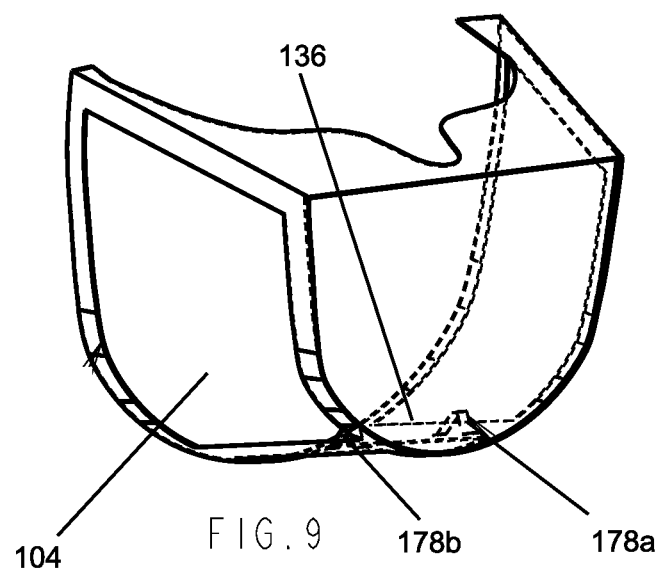
FIG. 9 is an isometric view of the inner layer of FIGS. 1 and 2.

FIG. 9 shows the inner layer 104 and the chin stops 178a and 178b provided within. The chin stops 178a and 178b extend superiorly from the inner filtering surface 136 and are adapted to engage a chin of a wearer. The chin stops 178a and 178b are also shown in FIGS. 11-13. As best shown in FIGS. 12 and 13, the first chin stop 178a is offset laterally from the second chin stop 178b. By engaging the chin of a wearer, the chin stops 178a and 178b help to secure the face mask 100 on the face of a wearer and help to prevent fogging by keeping the mouth of the wearer an appropriate distance from the inner front guard 134.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A face mask comprising:
   an outer layer having:
      an outer front guard constructed from a light-transmissive material,
      an outer filtering surface connected to and extending posteriorly from the outer front guard, the outer filtering surface including at least one outer air hole and a first face-adjacent edge, and
      an outer top connected to the outer front guard and the outer filtering surface three linear edges, the outer top including a first nose-adjacent edge,
      the outer front guard, the outer filtering surface, and the outer top defining an outer volume;
   an inner layer nestled within the outer volume of the outer layer, the inner layer having:
      an inner front guard separated from the outer front guard by a buffer space, the inner front guard being constructed from a light-transmissive material,
      an inner filtering surface connected to and extending posteriorly from the inner front guard, the inner filtering surface including at least one inner air hole and a second face-adjacent edge aligned with the first face-adjacent edge to form a combined face-adjacent edge, and an inner top connected to the inner front guard and the inner filtering surface, the inner top including a second nose-adjacent edge aligned with the first nose-adjacent edge to form a combined nose-adjacent edge; and a filter positioned between the outer filtering surface and the inner filtering surface, the filter covering the at least one outer air hole and the at least one inner air hole, and further comprising a seal extending along the combined face-adjacent edge and the combined nose-adjacent edge.

2. The face mask of claim 1, wherein the filter has a filtering surface area greater than or equal to 100 centimeters squared.

3. The face mask of claim 1, wherein the inner layer further comprises a chin stop extending superiorly from the inner filtering surface and adapted to engage a chin of a wearer.

4. The face mask of claim 3, wherein the chin stop is a first chin stop and the inner layer further comprises a second chin stop extending superiorly from the inner filtering surface, the second chin stop offset laterally from the first chin stop and also adapted to engage the chin of the wearer.

5. The face mask of claim 1 further comprising an eye shield extending superiorly from the outer layer planar with the outer front guard.

6. The face mask of claim 1, wherein the inner front guard and the outer front guard are arranged in parallel planes such that the buffer space is located between the parallel planes.

7. The face mask of claim 6, wherein a buffer distance extending perpendicularly between the parallel planes across the buffer space is greater than or equal to one millimeter.

8. The face mask of claim 1 further comprising a securement strap operably engaged with at least one of the outer layer and the inner layer to secure the face mask on a wearer.

9. The face mask of claim 8, wherein the securement strap is an upper securement strap and further comprising a lower securement strap.

10. The face mask of claim 1, wherein the outer layer is ultrasonically welded to the inner layer.

11. The face mask of claim 1, wherein the filter comprises a plurality of layers of nonwoven fabric.

12. The face mask of claim 11, wherein the plurality of layers includes an inner filter layer, a middle filter layer, and an outer filter layer.

13. The face mask of claim 12, wherein the face mask further includes a scan code printed on the outer filter layer and visible through the outer filtering surface.

14. The face mask of claim 1, wherein the outer filtering surface tapers conically outward from the outer front guard to the first face-adjacent edge.

15. The mask face of claim 1, wherein the inner filtering surface tapers conically outward from the inner front guard to the second face-adjacent edge.

16. The mask face of claim 1, wherein the combined nose-adjacent edge and the combined face-adjacent edge together form a mask perimeter, and the length of the mask perimeter is selected from a set of size options in order to accommodate a face size of a wearer of the mask.

17. The mask face of claim 16, wherein the combined nose-adjacent edge comprises a nose contour having a shape adapted to be flush against a nose of the wearer, the shape selected from a set of shape options in order to accommodate the nose shape of the wearer.

18. The mask face of claim 17, wherein the combined nose-adjacent edge further comprises two symmetric check contours.

\* \* \* \* \*